United States Patent
Orr (10) Patent No.: US 7,788,963 B2
(45) Date of Patent: Sep. 7, 2010

(54) SYSTEM AND METHOD FOR CALIBRATING A DETERMINATION OF PARTIAL PRESSURE OF ONE OR MORE GASEOUS ANALYTES

(75) Inventor: Joseph A. Orr, Park City, UT (US)

(73) Assignee: RIC Investments, LLC, Wilmington, DE (US)

(*) Notice: Subject to any disclaimer, the term of this patent is extended or adjusted under 35 U.S.C. 154(b) by 495 days.

(21) Appl. No.: 11/924,701

(22) Filed: Oct. 26, 2007

(65) Prior Publication Data

US 2008/0098795 A1   May 1, 2008

Related U.S. Application Data

(60) Provisional application No. 60/855,584, filed on Oct. 31, 2006.

(51) Int. Cl.
  *G01N 21/00*   (2006.01)
(52) U.S. Cl. .......................... 73/1.06; 73/1.59
(58) Field of Classification Search ............ None
  See application file for complete search history.

(56) References Cited

U.S. PATENT DOCUMENTS 4,854,153 A  8/1989  Miyagawa et al.
6,616,896 B2  9/2003  Labuda et al.
6,632,402 B2  10/2003  Blazewicz et al.
6,699,202 B1  3/2004  Gambert et al.
2003/0099574 A1  5/2003  Bentsen et al.

OTHER PUBLICATIONS

U.S. Appl. No. 11/805,074, May 22, 2007, Russell.

*Primary Examiner*—Robert R Raevis (57) ABSTRACT

One aspect of the invention relates to a system adapted to calibrate a determination of information related to one or more gaseous analytes in a body of gas being delivered to an objective by a gas source. In one embodiment the system comprises a partial pressure sensor, a total pressure monitor, a partial pressure module, and a calibration module. The partial pressure sensor generates an output signal related to the partial pressure of the one or more gaseous analytes in the body of gas. The total pressure monitor determines the total pressure of the body of gas. The partial pressure module determines the partial pressure of the one or more gaseous analytes in the body of gas according to a partial pressure function, wherein the partial pressure function describes the partial pressure of the one or more gaseous analytes in the body of gas as a function of the output signal generated by the partial pressure sensor. The calibration module that calibrates the partial pressure module by determining the partial pressure function.

25 Claims, 4 Drawing Sheets

SYSTEM AND METHOD FOR CALIBRATING A DETERMINATION OF PARTIAL PRESSURE OF ONE OR MORE GASEOUS ANALYTES

CROSS-REFERENCE TO RELATED APPLICATIONS

This application claims priority under 35 U.S.C. §119(e) from provisional U.S. patent application No. 60/855,584 filed Oct. 31, 2006 the contents of which are incorporated herein by reference.

BACKGROUND OF THE INVENTION

1. Field of the Invention

The invention relates to calibrating a system that determines information related to one or more gaseous analytes in a body of gas.

2. Description of the Related Art

Systems that determines information, for example a partial pressure, a concentration, a pressure fraction, etc., related to one or more gaseous analytes in a body of gas being delivered to the airway of a patient are known. For example, it is known to detect an oxygen concentration as the gaseous analyte being monitored by providing an oxygen sensor in-line in a patient circuit. In this typical configuration, one end of the patient circuit is coupled to a ventilator or other pressure support device and the end of the patient circuit is coupled to the airway of the patient. The oxygen sensor is located in the patient circuit between the ventilator and the airway of the patient, typically proximal to the airway of the patient.

Typically, over time, the accuracy of these sensors is degraded by "drift." Drift is the variability over time of the sensor response to its corresponding stimulus (e.g., the one or more gaseous analytes). Drift may be caused by a variety of factors. For example, drift may be caused by deterioration in components of a sensor, fluctuations in ambient conditions, mechanical inconsistencies (e.g., displacement of sensor components do to wear-and-tear over time), and/or other factors.

While in some instances, mechanisms and techniques for calibrating and/or recalibrating of these systems exist, this is often a cumbersome task that may adversely impact the patient being treated by the mechanical ventilation. For example, a typical sensor calibration process may require that the gaseous analyte monitoring system, for example, the oxygen sensor, be disengaged from the patient and/or a gas source supplying the flow of gas to the patient. This may require cessation of the treatment being received by the patient, which may be inconvenient and/or impractical.

In some cases, conventional calibration solutions may require additional equipment and/or resources, such as sample gaseous mixtures, external processing capabilities, and/or other equipment or resources in order to conduct the sensor calibration. The requirement of additional equipment and/or resources may impede the convenience and/or practicality of accurately calibrating the sensor. Other drawbacks associated with known calibration solutions for sensors that determine information related to one or more gaseous analytes in a body of gas also exist.

SUMMARY OF THE INVENTION

Accordingly, it is an object of the present invention to provide a system adapted to calibrate a determination of information related to one or more gaseous analytes in a body of gas being delivered to an objective by a gas source that overcomes the shortcomings of conventional calibration system. This object is achieved according to one embodiment of the present invention by providing a system that comprises a partial pressure sensor, a total pressure monitor, a partial pressure module, and a calibration module. The partial pressure sensor generates an output signal related to the partial pressure of the one or more gaseous analytes in the body of gas. The total pressure monitor determines the total pressure of the body of gas. The partial pressure module determines the partial pressure of the one or more gaseous analytes in the body of gas according to a partial pressure function. The partial pressure function describes the partial pressure of the one or more gaseous analytes in the body of gas as a function of the output signal generated by the partial pressure sensor.

The calibration module that calibrates the partial pressure module by determining the partial pressure function. In some instances, the calibration module determines the partial pressure function based on (i) a plurality of samples of the output signal generated by the partial pressure sensor at a plurality of points in time during a calibration time period, (ii) a plurality of determinations of the total pressure of the body of gas made at substantially the same points in time at which the plurality of samples of the output signal were generated, and (iii) a target concentration of the one or more analytes in the body of gas during the calibration time period. In some instances, the calibration time period comprises a time period during which the body of gas is being delivered to the objective while the gas source operates to keep the concentration of the one or more analytes in the body of gas substantially equal to the target concentration as the total pressure of the body of gas changes.

Another aspect of the invention relates to a method of calibrating a system that determines information related to one or more gaseous analytes in a body of gas being delivered to an objective by a gas source. In one embodiment, the system comprises the steps of generating an output signal that is related to a partial pressure of the one or more analytes in the body of gas and taking a plurality of samples of the output signal at a plurality of points in time during a calibration time period. The calibration time period comprises a time period during which the body of gas is being delivered to the objective while the gas source operates to keep the concentration of the one or more analytes in the body of gas substantially equal to the target concentration as the total pressure of the body of gas changes. The method further includes determining the total pressure of the body of gas at substantially the same points in time that the plurality of output signal samples are taken and determining a partial pressure function that describes the partial pressure of the one or more analytes in the body of gas as a function of the output signal, the partial pressure function being determined based on (i) the plurality of samples, (ii) the determinations of the total pressure of the body of gas made at substantially the same points in time at which the plurality of samples of the output signal were taken, and (iii) the target concentration of the one or more analytes in the body of gas during the calibration time period.

Another aspect of the invention relates to a method of calibrating a system that determines information related to one or more gaseous analytes in a body of gas contained in a conduit. In one embodiment, the method comprises generating an output signal that is related to a partial pressure of the one or more analytes in the body of gas; substantially containing the body of gas within the conduit; changing the total pressure of the body of gas within the conduit; taking a plurality of samples of the output signal at a plurality of points in time during a calibration time period. The calibration time period comprises the time period during which the total pressure of the body of gas within the conduit is being changed. The method further includes determining the total pressure of the body of gas at substantially the same points in time that the plurality of output signal samples are taken at and determining a partial pressure function that describes the partial pressure of the one or more analytes in the body of gas as a function of the output signal, the partial pressure function being determined based on (i) the plurality of samples, (ii) the determinations of the total pressure of the body of gas made at substantially the same points in time at which the plurality of samples of the output signal were taken, and (iii) the concentration of the one or more analytes in the body of gas during the calibration time period.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
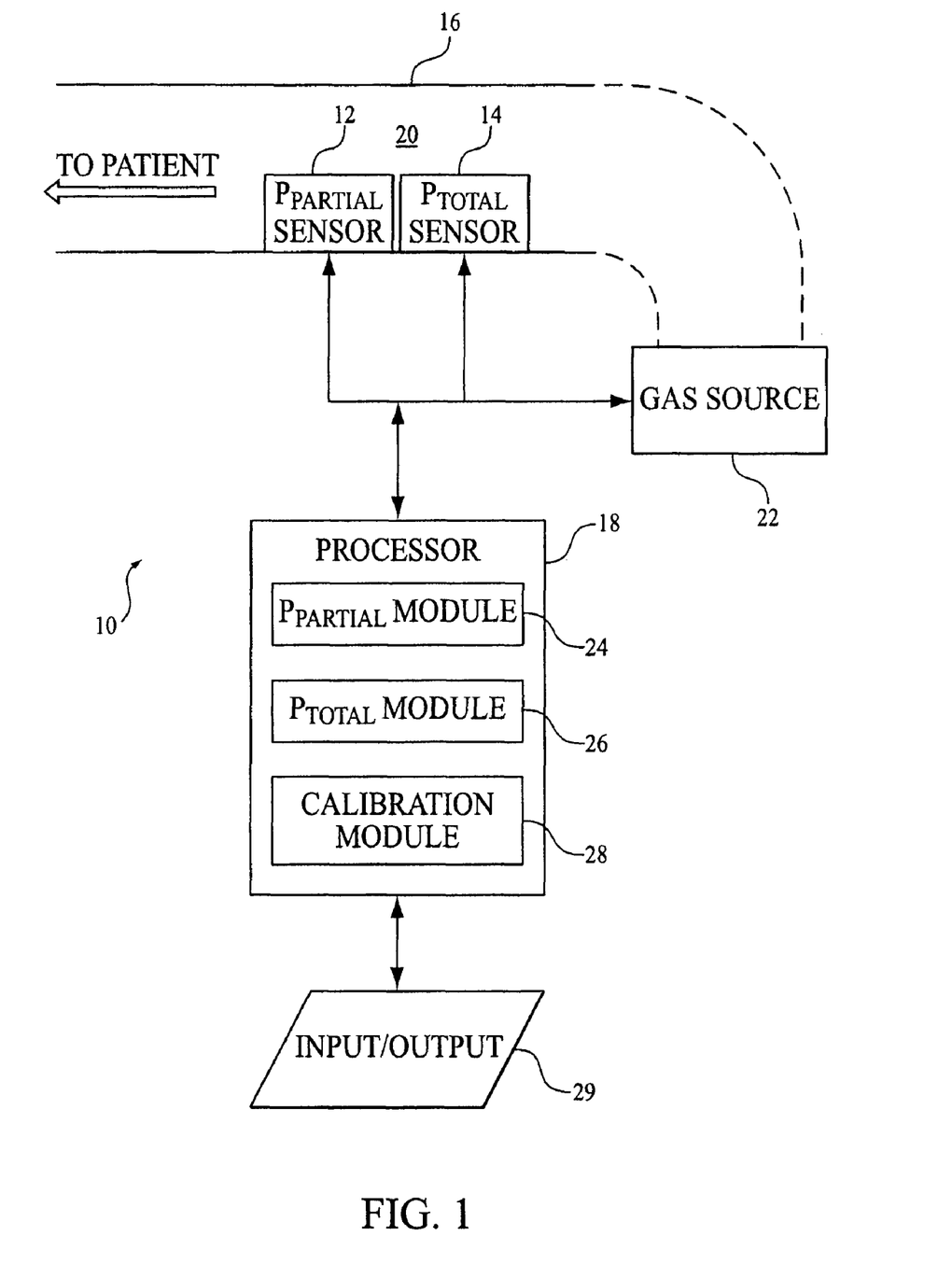
FIG. 1 illustrates a system adapted to calibrate a determination of information related to one or more gaseous analytes in a body of gas, according to one embodiment of the invention.

Turning to FIG. 1, a system 10 configured to determine information related to one or more analytes in a body of gas is illustrated. System 10 includes a partial pressure sensor 12, a total pressure sensor 14, a conduit 16, and a processor 18. Conduit 16 forms a flow path 20 through which a body of gas may pass. In an exemplary embodiment, conduit 16 is an airway adapter that is selectably located in-line in the patient circuit that connects a gas source 22 to the patient. Partial pressure sensor 12 and total pressure sensor 14 generate output signals that processor 18 uses to determine a partial pressure (or concentration) of one or more gaseous analytes included in the body of gas in flow path 20 and a total pressure of the body of gas in flow path 20, respectively.

In one embodiment, conduit 16 is adapted to carry gas to and/or from a patient. In a more particular example, conduit 16 may cooperate with a patient interface appliance configured to communicate with an airway of the patient. Some examples of the patient interface appliance may include, for example, an endotracheal tube, a nasal cannula, a tracheotomy tube, a nasal mask, a nasal/oral mask, a full face mask, a total face mask, or other patient interface appliances that communication a flow of gas with an airway of a patient. The present invention is not limited to these examples, and contemplates determination of analytes in any body of gas using any conventional patient interface appliance and conduit.

Conduit 16 may be operatively coupled to a gas source 22 to receive gas therefrom. In such embodiments, gas source 22 may control one or more properties of the gas provided to conduit 16. For example, gas source 22 may control a flow rate, a total pressure, a composition, and/or other properties of the gas in the conduit. In one embodiment, gas source 22 may comprise a ventilator (invasive or non-invasive) that provides pressurized, oxygenated gas to conduit 16. In another embodiments, the gas source is a pressure support system, such as a CPAP, bi-level, or auto-titration device, all of which provide a flow of breathing gas to an airway of a patient.

As was mentioned above, total pressure sensor 14 may generate one or more output signals that are related to a total pressure of the body of gas present in flow path 20. In one embodiment, total pressure sensor 14 may include an absolute pressure sensor that generates one or more output signals related to an absolute pressure of the body of gas. In other embodiments, total pressure sensor 14 may include a differential pressure that determines a pressure differential between a baseline pressure (e.g., pressure at ambient atmosphere, ambient pressure at sea level, etc.) and the pressure of the body of gas in flow path 20. Total pressure sensor 14 may include a Bourdon pressure sensor, a bellows pressure sensor, a secondary transducer pressure sensor, a thermal conductivity pressure sensor, a hot cathode pressure sensor, a cold cathode pressure sensor, a diaphragm pressure sensor, and/or other pressure sensors. For example, in one embodiment, total pressure sensor 14 may include the diaphragm pressure sensor disclosed in co-pending U.S. patent application Ser. No. 11,805,074 entitled "Airway Adapter with Optical Pressure Transducer and Method of Manufacturing a Sensor Component," filed May 22, 2007 ("the '074 application), the contents of which are hereby incorporated into this disclosure by reference. Total pressure sensor 14 may be located within conduit 16, removably securable from conduit 16, or in fluid communication with conduit 16 via tubing.

Partial pressure sensor 12 may generate one or more output signals related to a partial pressure of one or more analytes present in the body of gas in flow path 20. In one embodiment, the one or more output signals generated by partial pressure sensor 12 may be related to a partial pressure of oxygen in the body of gas. In another embodiment, the one or more output signals generated by partial pressure sensor 12 may be related to a partial pressure of an inhaled anesthetic such as nitrous oxide in the body of gas. Other exemplary inhaled anesthetics include the anesthetic agents halothane, isoflurane, enflurane, sevoflurane, and desflurane. Partial pressure sensor 12 may include one or more of a variety of different types of partial pressure sensors. For example, partial pressure sensor 12 may include a luminescence-quenching partial pressure sensor. In one embodiment, the luminescence-quenching partial pressure sensor may include the partial pressure sensor described in U.S. Pat. No. 6,616,896 to Labuda et al., entitled "Oxygen Monitoring Apparatus," issued Sep. 9, 2003 (hereafter "the '896 patent"). In one embodiment, the luminescence-quenching partial pressure sensor may include the partial pressure sensor described in U.S. Pat. No. 6,632,402 to Blazewicz et al., entitled "Oxygen Monitoring Apparatus," issued Oct. 14, 2003 (hereafter "the '402 patent"). Both of the '896 patent and the '402 patent are hereby incorporated into this disclosure by reference.

As can be seen in FIG. 1, sensors 12 and 14 are operatively linked with processor 18. This operative link may be accomplished by any mechanism that enables the output signals (or information related to the output signals) generated by sensors 12 and 14 to be transmitted to processor 18. For example, this communication may be accomplished via a wireless communications link and/or a wired communications link. The connection between sensors 12, 14 and processor 18 may include a discrete connection, a networked connection, and/or other connections.

The present invention further contemplates that processor 18 and one or both of sensors 12 and 14 (or components thereof) are disposed in a common housing. For example, energy emitters and detectors can be provided in a sensor "head" along with processor 18 that mounts onto an airway adapter. This airway adapter provides a sample site, for example by carrying a luminescable material, that is monitored by the sensing components in the sensor head. An input/output device 29 can be provided by communication information to and from processor 18. The present invention further contemplates that the functions and features of processor 18 and gas source 22 can be combined. For example, processor 18 can be implemented in a ventilator, so that the ventilator can perform the functions of processor 18.

Processor 18 determines a total pressure of the body of gas in flow path 20 and a partial pressure of one or more analytes within the body of gas based on the output signals generated by sensors 14 and 12, respectively. It should be appreciated that although processor 18 is shown in FIG. 1 as a single entity, this is for illustrative purposes only. In some implementations, processor 18 may include a plurality of processing units. These processing units may be physically located within the same device, or processor 18 may represent processing functionality of a plurality of devices operating in coordination. In instances in which a plurality of devices are implemented, operative communications links may be formed between the devices to enable communication and coordination therebetween.

For example, in some embodiments, processor 18 may include one or more processors external to system 10 (e.g., a host computer that communicates with system 10), one or more processors that are included integrally in one or more of the components of system 10, or both. Processors external to system 10 may, in some cases, provide redundant processing to the processors that are integrated with components in system 10, and/or the external processor may provide additional processing to determine additional information related to the one or more analytes in the body of gas in flow path 20.

As is shown in FIG. 1, in one embodiment processor 18 includes a partial pressure module 24, a total pressure module 26, and a calibration module 28. Modules 24, 26, and 28 may be implemented in software; hardware; firmware; some combination of software, hardware, and/or firmware; and/or otherwise implemented. It should be appreciated that although modules 24, 26, and 28 are illustrated in FIG. 1 as being co-located within a single processing unit, in implementations in which processor 18 includes multiple processing units, modules 24, 26, and/or 28 may be located remotely from the other modules and operative communication between modules 24, 26, and/or 28 may be achieved via one or more communication links. Such communication links may be wireless or hard wired.

Total pressure module 26 functions in cooperation with total pressure sensor 14 as a total pressure monitor that determines the total pressure of the body of gas in flow path 20. More particularly, total pressure module 26 determines the total pressure of the body of gas in flow path 20 based on the one or more output signals generated by total pressure sensor 14.

Partial pressure module 24 functions in cooperation with partial pressure sensor 12 as a partial pressure monitor that determines the partial pressure of one or more analytes present in the body of gas within flow path 20. Specifically, partial pressure module 24 determines the partial pressure of the one or more analytes in the body of gas in flow path 20 based on the one or more output signals generated by partial pressure sensor 12. In one embodiment, partial pressure module 24 determines the partial pressure of the one or more analytes according to a predetermined partial pressure function. The partial pressure function describes the partial pressure of the one or more analytes as a function of the one or more output signals generated by partial pressure sensor 12. In one embodiment, the partial pressure function may be a first order polynomial. For example, the partial pressure function may be represented as follows:

$$P_{partial}(s) = s \cdot \text{span} + \text{offset}; \tag{1}$$

where "$P_{partial}(s)$" represents the partial pressure of the one or more analytes, "s" represents one or more properties of the output signal(s) generated by partial pressure sensor 12 (e.g., a phase difference between output signals, a magnitude of the output signal(s), a modulation of the output signal(s), etc.), "span" represents a "span factor" of partial pressure sensor 12, and "offset" represents an offset of partial pressure sensor 12. More specifically, the "offset" includes a representation of the one or more properties of the output signal(s) generated by partial pressure sensor 12 when the partial pressure of the one or more analytes is zero.

Due to one or more of a variety of reasons, one or more of the parameters of the partial pressure function may "drift," or vary over time. For example, in embodiments in which the partial pressure function provided in equation (1) is implemented, one or both of the span factor and the offset of partial pressure sensor 12 may drift. Drift in one or more of the parameters of the partial pressure function, such as the span factor and/or offset of equation (1), may be caused by one or more of a variety of factors. For example, deterioration in components of partial pressure sensor 12, fluctuations in ambient conditions, mechanical inconsistencies (e.g., displacement of sensor components do to wear-and-tear over time), and/or other factors may cause one or more of the parameters of the partial pressure equation to drift. Partial pressure sensor 12 may require calibration or re-calibration due to variability in the chemistry of the luminescence quenching.

Calibration module 28 calibrates partial pressure module 24 by determining the partial pressure function used by partial pressure module 24 to determine the partial pressure of the one or more analytes. In some instances, calibration module 28 calibrates partial pressure module 24 in situ. In other words, calibration module may calibrate partial pressure module 24 without disconnecting conduit 16 (the airway adapter) from one or both of gas source 22 and an objective to which gas is being delivered to from gas source 22 by conduit 16 (e.g., a patient receiving gas from gas source 22). In one embodiment, this includes calibrating partial pressure module 24 during normal operation of system 10 (e.g., while gas is being delivered to the objective). As a result of this capability, the usability of system 10 is enhanced because the amount of system down time during which partial pressure module 24 is being calibrated is reduced. In some instances, calibration module 28 may enable partial pressure module 24 to be calibrated without additional equipment (e.g., without a calibration gas sample that includes known concentrations of the one or more analytes, without additional processing capacity, etc.). This may facilitate an initial calibration of partial pressure module 24 performed prior to connecting conduit 16 to gas source 22, and/or other calibrations of partial pressure module 24.

In one embodiment, calibration module 28 determines the partial pressure function based on measurements of the total pressure of the body of gas based on the output signal(s) generated by total pressure sensor 14 (which is less susceptible to drift than partial pressure sensor 12) and the following relationship between partial pressure and total pressure:

$$\text{fraction} = P_{partial} / P_{total}; \quad (2)$$

where "fraction" represents the pressure fraction of the one or more analytes in the body of gas (e.g., an oxygen fraction wherein the one or more analytes includes oxygen, a nitrous oxide fraction wherein the one or more analytes includes nitrous oxide, etc.), "$P_{partial}$" represents the partial pressure of the one or more analytes, and "$P_{total}$" represents the total pressure of the one or more analytes in the body of gas. Additionally, conventional gas measurement systems report gas fraction (i.e. concentration typically expressed in percent or volume percent) from Ppartial and barometric pressure (Pbaro) and as such are susceptible to pressure variations within the conduit during the breathing cycle. Computing concentration using Ptotal instead of Pbaro would alleviate the problems associated with pressure variations with the breathing circuit.

In order to leverage the measurements of the total pressure of the body of gas based on the output signal(s) generated by total pressure sensor 14 and the relationship described by equation (2), calibration module 28 takes advantage of situations in which the pressure fraction of the one or more analytes in the body of gas is known and/or remains substantially constant while the pressures of the body of gas is changing. For example, in the embodiment in which gas source 22 comprises a ventilator designed to deliver the body of gas to an airway of a patient, the ventilator will control the delivery of the body of gas such that during inspiration by the patient the concentration of one or more analytes in the body of gas (e.g., oxygen, nitrous oxide, anesthetic agents etc.) will remain substantially fixed at a target concentration. For example, many conventional ventilators include a supplemental gas supply (such as an oxygen supply) and a blender that allows the user to set and maintain the oxygen fraction ($FIO_2$) of the gas delivered to the patient at a given or target level over multiple respiratory cycles.

As the patient inspires the delivered gas, the pressure of the body of gas in flow path 20 will fluctuate (e.g., increase or decrease). Further, the target concentration of the one or more analytes in the body of gas is a value that is known to the ventilator. The target concentration may be expressed in terms of a corresponding pressure fraction of the one or more analytes in the body of gas.

In some embodiments in which gas source 22 includes a ventilator, processor 18 may be operatively linked with gas source 22 to receive information related to the target concentration of the one or more analytes in the body of gas being delivered to an airway of the patient (e.g., the target concentration, the corresponding pressure fraction of the one or more analytes in the body of gas, etc.). In one embodiment, processor 18 also receives information as to the timing of one or more inspirations by the patient (e.g., a start of an inspiration, an end of an inspiration, a duration of an inspiration, etc.). Calibration module 28 then implements the information received from gas source 22, the total pressure of the body of gas determined by total pressure module 26, and the output signal(s) generated by partial pressure sensor 12 to determine the partial pressure function.

More particularly, in one embodiment, calibration module 28 determines the partial pressure function by (1) determining partial pressures of the one or more analytes based on the target concentration of the one or more analytes, e.g., the set $FIO_2$ to be provided by the ventilator, and measurements of total pressure determined by total pressure module 26 at a plurality of points in time during an inspiration of the patient, and (2) comparing the determined partial pressures of the one or more analytes with the output signal(s) generated by partial pressure sensor 12 at points in time that are substantially contemporary with the points in time for which the total pressure of the body of gas has been determined.

Figure 2:
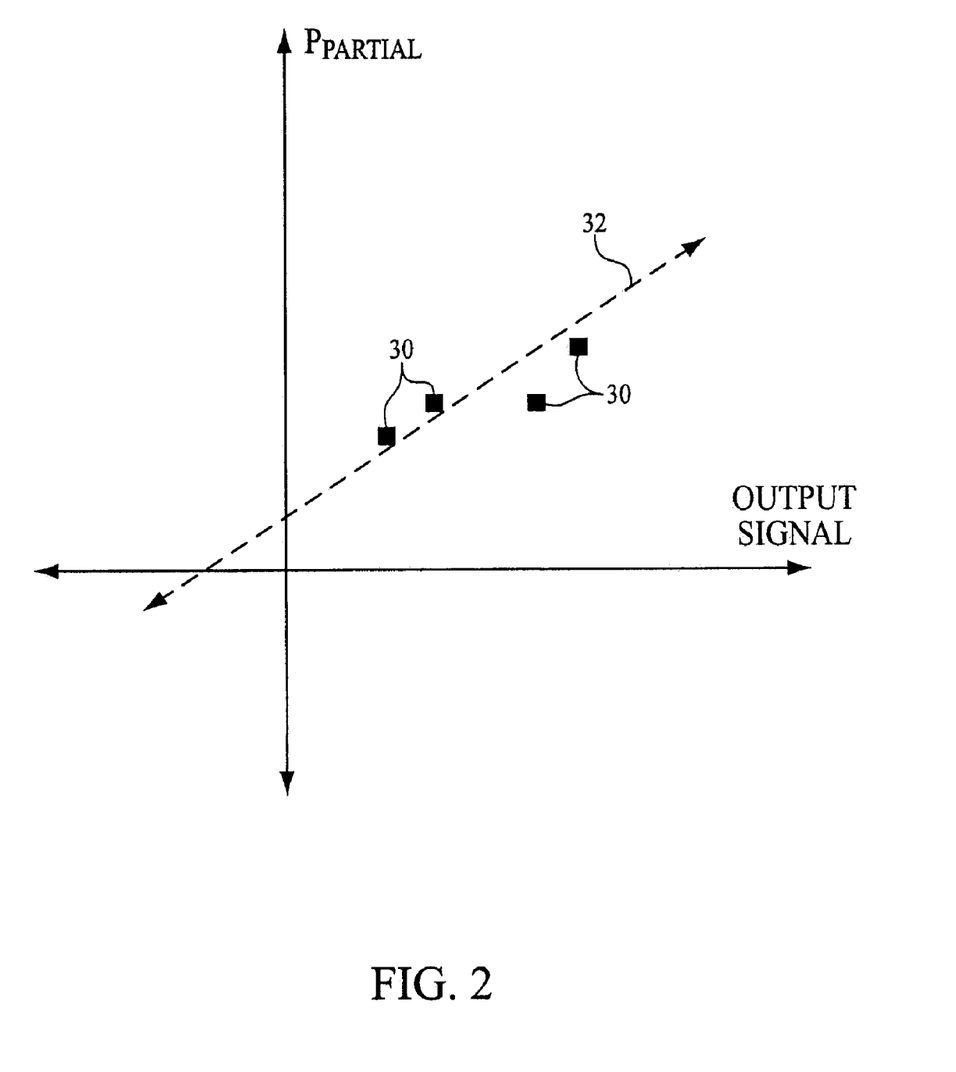
FIG. 2 illustrates a plot of partial pressure in terms of output signals generated by a partial pressure sensor, in accordance with one embodiment of the invention.

FIG. 2 illustrates one example of how the determined partial pressures may be compared with the output signal(s) to determine the partial pressure function. As can be seen, FIG. 2 includes a two-dimensional plot with the horizontal axis assigned to one or more of the properties of the output signal (s) generated by partial pressure sensor 12 (e.g., a phase difference between output signals, a magnitude of the output signal(s), a modulation of the output signal(s), etc.), and the vertical axis assigned to the partial pressures determined based on the total pressures determined by total pressure module 26, the target concentration, and the relationship represented in equation (2).

The illustration of the two-dimensional plot shown in FIG. 2 also includes a plurality of plot points 30. Each of plot points 30 represents a point of time at which the output signal(s) generated by partial pressure sensor 12 has been sampled and the total pressure of the body of gas has been determined by total pressure module 26. In one embodiment, to determine the partial pressure function, a curve 32 may be determined by fitting curve 32 to plot points 30 using conventional curve-fitting techniques. The equation corresponding to curve 32 may then be used as the partial pressure function, as it may be written in a form that describes the vertical axis of the plot (e.g., the partial pressure of the one or more analytes) as a function of the horizontal axis of the plot (e.g., the one or more properties of the output signal(s) generated by partial pressure sensor 12). In one embodiment, curve 32 may be written as a first order polynomial in point-slope form, wherein the slope of the equation representing curve 32 is the span factor of partial pressure sensor 12 and the intercept value of equation representing curve 32 is the offset of partial pressure sensor 12.

It should be appreciated that the determination of the partial pressure function in this manner to calibrate partial pressure module 24 is merely one of a variety of techniques that implement the above-described relationships between the total pressures determined by total pressure module 26, the target concentration of the one or more analytes, and the partial pressure of the one or more analytes. For example, in one embodiment, the comparison of the set partial pressures determined based on the total pressures determined by total pressure module 26 and the target concentration with the output signal(s) generated by partial pressure sensor 12 includes determining a set of partial pressures based on the output signal(s) generated by partial pressure sensor 12 using an existing partial pressure function. The two sets of partial pressure determinations (e.g., one set based on determinations of total pressure by total pressure module 26 and the target concentration and one set based on the output signals generated by partial pressure sensor 12 and the partial pressure function) are then compared, and the existing partial pressure function is adjusted based on differences between the values for partial pressure in the two sets of partial pressure determinations.

In some embodiments, calibration module 28 is capable of calibrating partial pressure module 24 by determining the partial pressure function while conduit 16 is disconnected from gas source 22. For example, in one embodiment, calibration module 28 determines the partial pressure function without additional equipment outside of processor 18 (e.g., without gas from a gas source, without a calibration gas sample that includes known concentrations of the one or more analytes, without additional processing capability, etc.).

To accomplish this, calibration module 28 may use a known concentration of the one or more analytes in ambient atmosphere as the target concentration. In order to obtain determinations of total pressure by total pressure module 26 and samples of the output signal(s) generated by partial pressure sensor 12 at a plurality of total pressures, a user exposes conduit 16 to ambient atmosphere so that flow path 20 fills with atmospheric gas. Then, the user "squeezes" conduit 16 by sealing (or substantially sealing) the openings of conduit 16 and decreasing the volume of conduit 16. The volume of conduit 16 may be decreased, for example, by deforming an outer wall of conduit 16 (this would decrease the volume, thereby elevating the total pressure of the body of gas inside).

As the pressures of the body of gas within conduit 16 change as a result of the manipulation of conduit 16, the target concentration (e.g., the concentration of the one or more analytes in ambient atmosphere) remains substantially fixed as the body of gas is substantially contained within conduit 16. Therefore, total pressures determined by total pressure module 26, output signal(s) generated by partial pressure sensor 12, and the target concentration may be used as described above by calibration module 28 to determine the partial pressure function, thereby calibrating partial pressure module 24.

Figure 3:
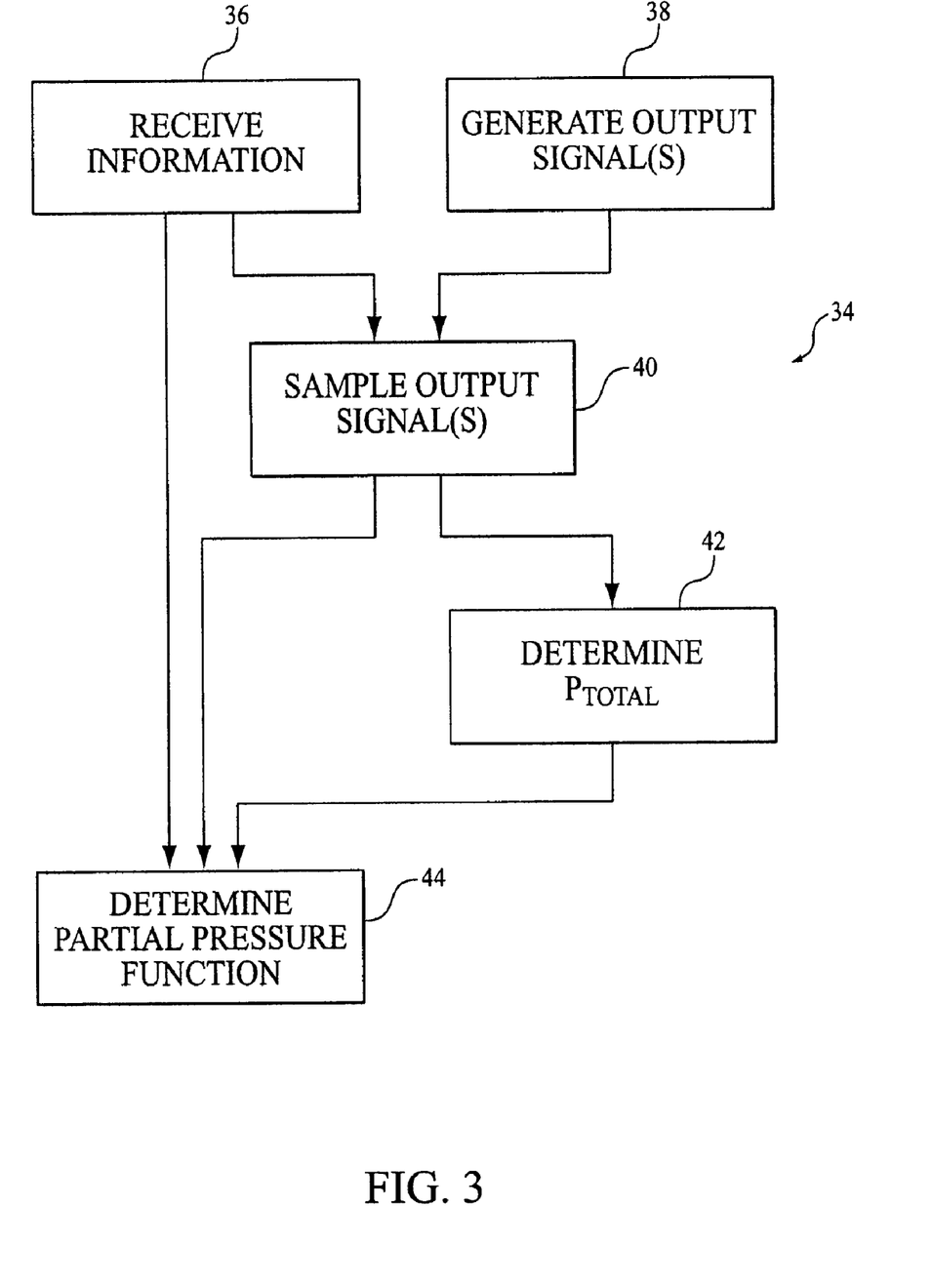
FIG. 3 illustrates a method of calibrating a system that determines information related to one or more gaseous analytes in a body of gas, according to on embodiment of the invention.

FIG. 3 illustrates a method 34 of calibrating a system that determines information related to one or more gaseous analytes in a body of gas. In one embodiment, the system delivers the body of gas to an airway of a patient from a gas source and the method enables the system to be calibrated while the body of gas is being delivered to the patient's airway. It should be appreciated that although specific reference is made below regarding various operations of method 34 that can be executed by components of system 10 (e.g., illustrated in FIG. 1 and described above), this is for illustrative purposes. In other embodiments, systems other than system 10 may be implemented to execute some or all of the operations of method 34.

Method 34 includes an operation 36 at which information related to the delivery of the body of gas to the patient is determined. Operation 36 may include determining a target concentration of the one or more analytes in the body of gas (such as the $FIO_2$ set via the ventilator), information related to a calibration time period (e.g., an inspiration start time, an inspiration end time, a length of inspiration, etc.), and/or other information related to the delivery of the body of gas. The calibration time period may include a period of time during which the concentration of the one or more analytes in the body of gas are anticipated to be substantially equal to the target concentration. In one embodiment, operation 36 may be executed by processor 18 in receiving information communicated from gas source 22 (e.g., as illustrated in FIG. 1 and described above).

At operations 38 and 40, one or more output signals that are related to a partial pressure of the one or more analytes in the body of gas are generated and sampled, respectively. For example, in one embodiment, the generation of the one or more output signals at operation 38 is performed by partial pressure sensor 12, and the sampling of the one or more generated output signals is executed by processor 18 (e.g., as illustrated in FIG. 1 and described above).

At an operation 42, the total pressure of the body of gas is determined at substantially the same points in time that the plurality of output signal samples are taken. In one embodiment, operation 42 includes the determination of total pressures by total pressure module 26 based on output signal(s) generated by total pressure sensor 14 (e.g., as illustrated in FIG. 1 and described above) at substantially the same points in time as the points in time at which the output signal samples are taken.

At an operation 44, a partial pressure function is determined. The partial pressure function describes the partial pressure of the one or more analytes in the body of gas based on the output signals generated at operation 38. In one embodiment, the partial pressure function is determined based on (1) the plurality of sample of the output signal(s) taken at operation 40, (2) the determinations of the total pressure of the body of gas made at operation 42, and (3) the target concentration. Operation 44 may be executed by calibration module 28 (e.g., as illustrated in FIG. 1 and described above).

Figure 4:
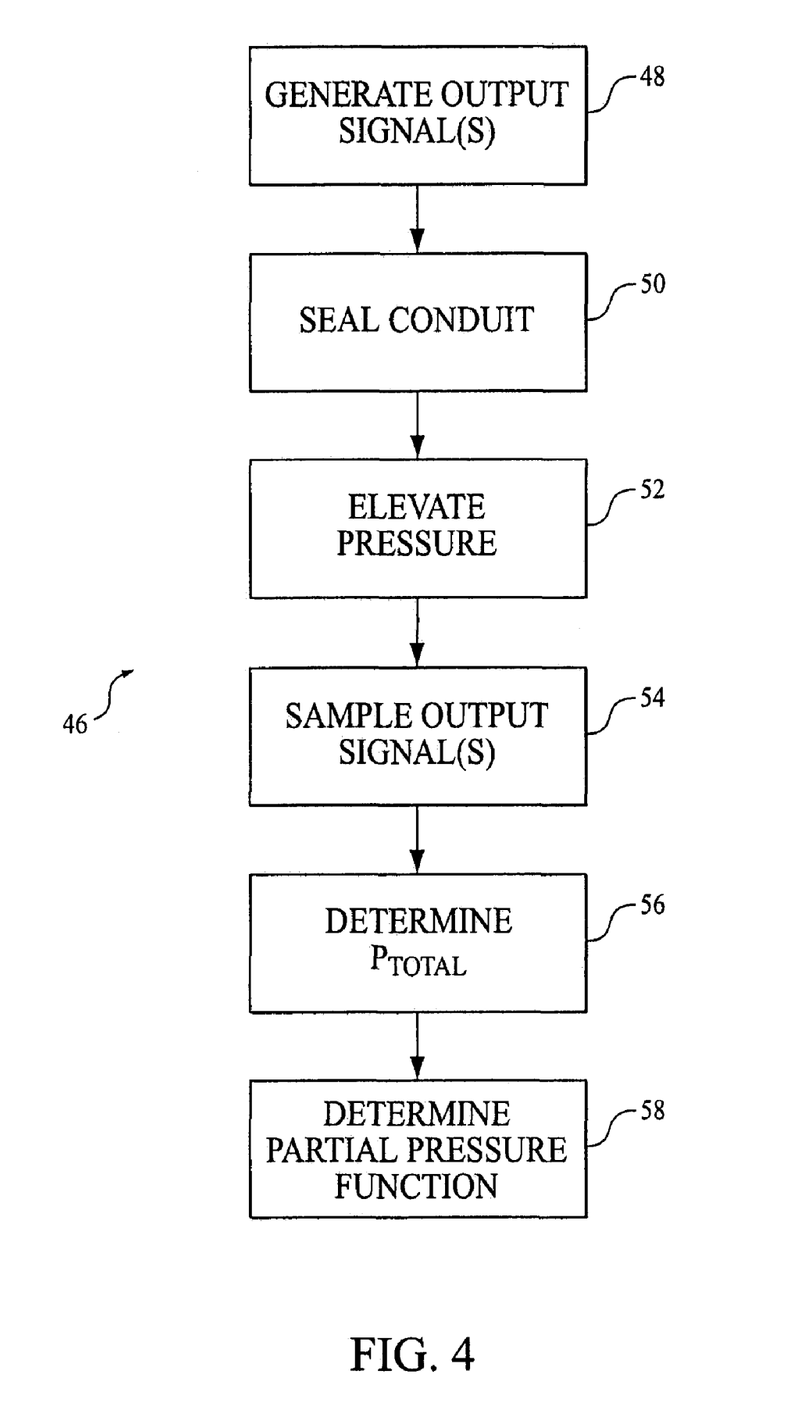
FIG. 4 illustrates a method of calibrating a system that determines information related to one or more gaseous analytes in a body of gas, according to on embodiment of the invention.

FIG. 4 illustrates a method 46 of calibrating a system that determines information related to one or more gaseous analytes in a body of gas contained in a conduit. It should be appreciated that although specific reference is made below regarding various operations of method 46 that can be executed by components of system 10 (e.g., illustrated in FIG. 1 and described above), this is for illustrative purposes. In other embodiments, systems other than system 10 may be implemented to execute some or all of the operations of method 46.

In one embodiment, method 46 includes an operation 48. At operation 48 one or more output signals are generated. The generated output signals are related to a partial pressure of the one or more analytes in the body of gas. In one embodiment, operation 48 is performed by partial pressure sensor 12 (e.g., illustrated in FIG. 1 and described above).

At an operation 50, the body of gas is substantially contained within the conduit. In one embodiment, operation 50 is executed by a user that manually seals the body of gas within the conduit by substantially sealing the openings defined by the conduit.

At an operation 52, the pressure of the body of gas within the conduit is changed. For example, the pressure of the body of gas within the conduit may be elevated by a user that manipulates the exterior of the conduit. In one embodiment, the manipulation of the exterior of the conduit includes the manual compression of an outer surface of the conduit. This can also be accomplished using gas source 22, for example, by causing the gas source to provide a pressure spike or surge to the ventilator (patient) circuit.

At an operation 54, the one or more output signals generated at operation 50 are sampled a plurality of points in time during a calibration time period. The calibration time period is the period of time during which the total pressure of the body of gas within the conduit is being changed. In one embodiment, operation 54 is performed by processor 18 (e.g., illustrated in FIG. 1 and described above).

At an operation 56, the total pressure of the body of gas is determined at substantially the same points in time as the points in time at which the plurality of output signal samples are taken. In one embodiment, operation 56 includes the determination of total pressures by total pressure module 26 based on output signal(s) generated by total pressure sensor 14 (e.g., as illustrated in FIG. 1 and described above) at substantially the same points in time as the points in time at which the output signal samples are taken.

At an operation 58, a partial pressure function is determined. The partial pressure function describes the partial pressure of the one or more analytes in the body of gas based on the output signals generated at operation 48. In one embodiment, the partial pressure function is determined based on (1) the plurality of sample of the output signal(s) taken at operation 54, (2) the determinations of the total pressure of the body of gas made at operation 56, and (3) a target concentration of the one or more analytes in the body of gas. The target concentration may be the concentration of the one or more analytes in ambient atmosphere. Operation 58 may be executed by calibration module 28 (e.g., as illustrated in FIG. 1 and described above).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system adapted to calibrate a determination of information related to one or more gaseous analytes in a body of gas being delivered to an objective by a gas source, the system comprising:
   a partial pressure sensor that generates an output signal related to the partial pressure of the one or more gaseous analytes in the body of gas;
   a total pressure monitor that determines the total pressure of the body of gas;
   a partial pressure module that determines the partial pressure of the one or more gaseous analytes in the body of gas according to a partial pressure function, wherein the partial pressure function describes the partial pressure of the one or more gaseous analytes in the body of gas as a function of the output signal generated by the partial pressure sensor; and
   a calibration module that calibrates the partial pressure module by determining the partial pressure function, wherein the calibration module determines the partial pressure function based on (i) a plurality of samples of the output signal generated by the partial pressure sensor at a plurality of points in time during a calibration time period, (ii) a plurality of determinations of the total pressure of the body of gas made at substantially the same points in time at which the plurality of samples of the output signal were generated, and (iii) a target concentration of the one or more analytes in the body of gas during the calibration time period, wherein the calibration time period comprises a time period during which the body of gas is being delivered to the objective while the gas source operates to keep the concentration of the one or more analytes in the body of gas substantially equal to the target concentration as the total pressure of the body of gas changes.

2. The system of claim 1, wherein the total pressure monitor comprises:
   a total pressure sensor that generates an output signal related to the total pressure of the body of gas; and
   a total pressure module that determines the total pressure of the body of gas based on the output signal generated by the total pressure sensor.

3. The system of claim 2, further comprising a processor that comprises the total pressure module, the partial pressure module, and the calibration module.

4. The system of claim 1, wherein the gas source comprises a ventilator.

5. The system of claim 1, wherein the calibration time period comprises at least a portion of an inspiration cycle of the patient.

6. The system of claim 1, wherein the one or more analytes in the body of gas comprise oxygen.

7. The system of claim 6, wherein the target concentration comprises an oxygen fraction of the body of gas.

8. The system of claim 1, wherein determining the partial pressure function comprises adjusting a previously determined partial pressure function.

9. The system of claim 1, wherein the objective comprises an airway of a patient.

10. The system of claim 1, wherein the total pressure comprises the sum of the a barometric pressure and a differential pressure.

11. A method of calibrating a system that determines information related to one or more gaseous analytes in a body of gas being delivered to an objective by a gas source, the method comprising:
   generating an output signal that is related to a partial pressure of the one or more analytes in the body of gas;
   taking a plurality of samples of the output signal at a plurality of points in time during a calibration time period, wherein the calibration time period comprises a time period during which the body of gas is being delivered to the objective while the gas source operates to keep the concentration of the one or more analytes in the body of gas substantially equal to the target concentration as the total pressure of the body of gas changes;
   determining the total pressure of the body of gas at substantially the same points in time that the plurality of output signal samples are taken; and
   determining a partial pressure function that describes the partial pressure of the one or more analytes in the body of gas as a function of the output signal, the partial pressure function being determined based on (i) the plurality of samples, (ii) the determinations of the total pressure of the body of gas made at substantially the same points in time at which the plurality of samples of the output signal were taken, and (iii) the target concentration of the one or more analytes in the body of gas during the calibration time period.

12. The method of claim 11, wherein the gas source comprises a ventilator.

13. The method of claim 11, wherein the calibration time period comprises at least a portion of an inspiration cycle of the patient.

14. The method of claim 11, wherein the one or more analytes in the body of gas comprise oxygen.

15. The method of claim 14, wherein the target concentration comprises an oxygen fraction of the body of gas.

16. The method of claim 11, wherein determining the partial pressure function comprises adjusting a previously determined partial pressure function.

17. The method of claim 11, wherein the objective comprises an airway of a patient.

18. The method of claim 11, wherein the total pressure comprises a sum of a barometric pressure and a differential pressure.

19. A method of calibrating a system that determines information related to one or more gaseous analytes in a body of gas contained in a conduit, the method comprising:
  generating an output signal that is related to a partial pressure of the one or more analytes in the body of gas;
  substantially containing the body of gas within the conduit;
  changing the total pressure of the body of gas within the conduit;
  taking a plurality of samples of the output signal at a plurality of points in time during a calibration time period, wherein the calibration time period comprises the time period during which the total pressure of the body of gas within the conduit is being changed;
  determining the total pressure of the body of gas at substantially the same points in time that the plurality of output signal samples are taken at; and
  determining a partial pressure function that describes the partial pressure of the one or more analytes in the body of gas as a function of the output signal, the partial pressure function being determined based on (i) the plurality of samples, (ii) the determinations of the total pressure of the body of gas made at substantially the same points in time at which the plurality of samples of the output signal were taken, and (iii) the concentration of the one or more analytes in the body of gas during the calibration time period.

20. The method of claim 19, wherein the concentration of the one or more analytes in the body of gas is known.

21. The method of claim 19, wherein the concentration of the one or more analytes in the body of gas is substantially equal to the concentration of the one or more analytes in ambient atmosphere.

22. The method of claim 19, wherein sealing the body of gas within the conduit and changing the total pressure of the body of gas within the conduit comprise manually sealing openings defined by the conduit and manipulating the exterior of the conduit to elevate the total pressure of the body of gas within the conduit.

23. The method of claim 19, wherein the one or more analytes comprise oxygen.

24. The method of claim 19, wherein determining the partial pressure function comprises adjusting a previously determined partial pressure function.

25. The method of claim 19, wherein the total pressure comprises a sum of a barometric pressure and a differential pressure.

* * * * *